United States Patent [19]
Sherman et al.

[11] Patent Number: 5,928,253
[45] Date of Patent: Jul. 27, 1999

[54] INTEGRATED CANNULA AND VASCULAR CLAMP ASSEMBLY

[75] Inventors: Benjamin Sherman, Milpitas; Dwight P. Morejohn, Davis, both of Calif.

[73] Assignee: Cardiothoracic Systems, Inc., Cupertino, Calif.

[21] Appl. No.: 09/040,230

[22] Filed: Mar. 13, 1998

[51] Int. Cl.⁶ .................................................. A61B 17/00
[52] U.S. Cl. ........................................ 606/151; 606/157
[58] Field of Search .................................... 606/157, 158, 606/151, 1, 211, 159, 205, 207; 604/908, 912

[56] References Cited

U.S. PATENT DOCUMENTS

| | | | |
|---|---|---|---|
| 5,236,437 | 8/1993 | Wilk et al. | 606/207 |
| 5,425,708 | 6/1995 | Nasu | 604/76 |
| 5,618,307 | 4/1997 | Donlon et al. | 606/205 |
| 5,624,454 | 4/1997 | Palti et al. | 606/151 |
| 5,683,405 | 11/1997 | Yacoubian et al. | 606/158 |
| 5,697,942 | 12/1997 | Palti | 606/151 |

OTHER PUBLICATIONS

Rationale for an extra–vascular aortic clamp, G. Champsaur, M.D. France.

*Primary Examiner*—Michael Buiz
*Assistant Examiner*—Vikki Trinh
*Attorney, Agent, or Firm*—Lyon & Lyon LLP

[57] ABSTRACT

The present invention relates to an integrated cannula and vascular clamp assembly. The integrated cannula and vascular clamp assembly includes a pair of clamping members made of a physiologically acceptable material that are pivotally coupled to a cannula for movement between an open position for at least partially surrounding a portion of a blood vessel section to be occluded and a clamping position for compressing the blood vessel with pressure sufficient to occlude blood flow through the section.

25 Claims, 5 Drawing Sheets

INTEGRATED CANNULA AND VASCULAR CLAMP ASSEMBLY

FIELD OF THE INVENTION

This invention relates generally to surgical instruments for temporarily occluding a blood vessel during surgical procedures, and more particularly to vascular clamps for temporarily occluding a blood vessel during cardiopulmonary bypass (CPB) to facilitate the performance of cardiac procedures.

BACKGROUND OF THE INVENTION

To facilitate the reader's understanding of the present invention, the CPB process is generally described below, followed by a description of the problems with vascular clamps used during the CPB process in the past.

The descriptive terms upstream and downstream, when used herein in relation to the patient's vasculature, refer to directions closer to and further from the heart in the arterial system, and the opposite in the venous system. The terms proximal and distal, when used herein in relation to instruments, refer to directions closer to and farther away from the operator of the instrument, respectively.

During CPB, it is desirable to provide life-support functions, a motionless, decompressed heart and a dry, bloodless field of view for the surgeon. In a basic CPB system, oxygen-poor blood is drained by means of gravity or is syphoned from the patient's venous circulation and is transported to a pump-oxygenator, commonly known as the heart-lung machine, where the blood is exposed to a gaseous mixture that eliminates carbon dioxide and adds oxygen to the blood. The oxygenated blood is then returned or perfused into the patient's arterial circulation for distribution throughout the entire body. This process requires a venous drainage cannula (or cannulae) to be placed into the right side of the heart (typically the right atrium) or directly in the major veins (typically the superior vena cava (SVC) and/or inferior vena cava (IVC)) or through peripheral vein access sites to drain unoxygenated blood from the patient and deliver it to the heart-lung machine. Similarly, an arterial or aortic perfusion cannula is placed in the aorta or another large peripheral artery, such as the common femoral artery, to return or perfuse oxygenated blood to the patient. The heart and lungs of the person can thereby be effectively bypassed, thus allowing the surgeon to operate on a bloodless heart.

The insertion of the arterial (aortic) perfusion cannula is usually performed in the following fashion. After an incision is made in the patient's chest and the pericardium (the protective sac around the heart) has been entered, two concentric purse string sutures are placed into the anterior wall of the ascending aorta just proximal to upstream of the brachiocephalic trunk. A "choker" tube or sleeve is positioned over the trailing ends of the suture threads to act as a tourniquet for tightening the purse string suture. A small incision is then made through the wall of the aorta into its lumen in the center of the purse-string sutures. The aortic perfusion cannula is then quickly inserted through that incision into the lumen of the aorta, taking care to minimize the escape of blood from the puncture site. The purse string sutures are then tightened by means of their respective tourniquets to seal the aortic wall around the perfusion cannula in order to prevent the escape of blood from the aorta. Air is then evacuated from the perfusion cannula as it is joined by a connector to the tubing from the pump-oxygenator. A mechanical cross-clamp, i.e., vascular clamp, is placed on the ascending aorta just downstream of the aortic root and upstream of the cannula to ensure that no blood flows back into the aorta during CPB.

The venous drainage cannula(e) is (are) inserted in a similar manner directly through an incision in the right atrium of the heart or into the superior and/or inferior vena cava for connection to the drainage side of the pump-oxygenator. Once the requisite cannulae are in place and the connections are made to the heart-lung machine, CPB is instituted by allowing unoxygenated blood returning to the right side of the heart to be diverted through the venous drainage cannula(e) and into the pump-oxygenator where it is oxygenated and temperature-adjusted. From there, the blood is pumped into the patient's arterial system via the arterial or aortic perfusion cannula to provide oxygen rich blood to the patient's body and brain.

After CPB has been established, the process known as cardioplegia, which literally means "heart stop," is used to arrest the beating of the heart, and in some procedures, to provide oxygen to the myocardium. Cardioplegia is administered by delivering a cardioplegic solution, such as potassium, magnesium, procaine, or a hypoclacemic solution, to the myocardium by antegrade and/or retrograde perfusion. For example, cardioplegia may be administered by inserting a needle into the aorta upstream of the aortic cross-clamp and injecting cardioplegic solution into the aortic root. The cardioplegic solution drains in the normal direction of blood flow into the coronary ostia, through the coronary arteries, and into the capillaries within the myocardium.

The problems with conventional vascular clamps used during the CPB process will now be described. As previously mentioned, the vascular cross-clamp is placed externally on the ascending aorta through an incision or opening in the chest. Traditionally, when cardiac procedures are to be performed, the sternum is cut longitudinally (a median sternotomy), providing access between opposing halves of the anterior portion of the rib cage to the heart and other thoracic vessels and organs. Alternatively, a lateral thoracotomy is formed, wherein a large incision is made between two ribs. A portion of one or more ribs may be permanently removed to optimize access. Either of these techniques provides a substantial opening in the chest, giving the surgeon a relatively large working area through which to operate.

A problem with these techniques for accessing the heart area is that they cause the patient significant trauma. The patient requires immediate postoperative care in an intensive care unit, a total period of hospitalization of up to seven to ten days, and a recovery period that can be as long as six to eight weeks.

In more modern, minimally invasive cardiac surgery, smaller incisions are made in the chest at various strategic locations. The surgical instruments are introduced at these locations. An endoscope is provided at one of these locations, and selected surgical instruments are manipulated by the surgeon with the aid of the endoscope. Accessing the heart area with minimally invasive techniques causes the patient less trauma than the techniques described previously.

A problem with all of the aforementioned techniques for accessing the heart area, especially minimally invasive techniques, is that the access area or the incision area is very limited in size. The larger and/or the greater the number of surgical instruments, the more they interfere with the cardiac procedures to be performed.

Vascular clamps in the past have traditionally had long and/or large shafts and handles that tend to obstruct the access area during cardiac surgery. Some vascular clamps in the past have included "bulldog" clamps, or similar clamps, to alleviate this problem. A "bulldog" clamp is a small V-shaped clamp that is applied to a blood vessel with an applier, such as forceps, and left on the blood vessel until it needs to be removed. Once the "bulldog" clamp is applied to the blood vessel, the applier is removed from the operating site, reducing the interfering effect the cross-clamp has on the surgical procedure. A problem with "bulldog" clamps and related clamps is that they do not give the operator immediate control over the opening and closing of the clamp. If the clamp needs to be opened, an instrument, usually different than the applier, must be delivered to the surgeon, introduced through the incision, and used to remove the clamp. This opening process takes too long if blood flow through the clamped blood vessel is immediately necessary.

A need therefore exists for a vascular clamp that does not take up a significant amount of space at the operating site, yet provides the operator with immediate control over the clamp.

A problem with vascular clamps that relates more to minimally invasive cardiac procedures is that they typically have a construction that makes them difficult to introduce through a narrow insertion in the chest, and, once in the chest, they are difficult to manipulate around body tissue to the blood vessel to be clamped.

In the past, vascular clamps, once they were clamped to the blood vessel, are usually held in the closed position manually by the operator, or with a locking mechanism. Manually maintaining the clamp in the closed position is desirable in that it gives the operator a better feel for the pliability of the blood vessel; however, it also introduces the possibility of operator error. For example, too much pressure on the blood vessel will damage the blood vessel, and insufficient pressure will not preclude blood flow through the blood vessel. Particularly for clamps without attached handles, quick removal of the clamp is difficult if blood flow through the blood vessel becomes immediately necessary.

Therefore, a further need exists for a vascular clamp that includes a locking mechanism that allows for the immediate release of the clamp.

SUMMARY OF THE INVENTION

An aspect of the present invention involves an integrated cannula and vascular clamp assembly for delivering fluid to a blood vessel and temporarily occluding a section of the blood vessel. The integrated cannula and vascular clamp assembly has a cannula made of a physiologically acceptable material for delivering fluid to a blood vessel. The cannula includes a frame, and an elongated cannula tube with a distal tip supported by the frame. The cannula tube is adapted to deliver fluid to the blood vessel through the distal tip. A pair of clamping members made of a physiologically acceptable material are pivotally coupled to the frame for movement apart from each other to an open position for at least partially surrounding a portion of the blood vessel section to be occluded and towards each other to a clamping position for compressing the blood vessel with pressure sufficient to occlude blood flow through the section. The integrated cannula and vascular clamp assembly simplifies the cardiac procedure and reduces the obstructing effect and space requirements that a separate vascular clamp has on the cardiac procedure.

The integrated cannula and vascular clamp assembly includes a locking mechanism adapted to maintain the clamping members in the clamping position and may include a quick release mechanism adapted to disengage the locking mechanism upon actuation of the quick release mechanism, allowing immediate movement of the clamping members.

Another aspect of the present invention involves a method of applying an integrated cannula and vascular clamp assembly to a blood vessel. The method includes a number of steps, one of which is providing an integrated cannula and vascular clamp assembly with a cannula made of a physiologically acceptable material for delivering fluid to the blood vessel. The cannula includes a frame, and an elongated cannula tube with a distal tip supported by the frame. A pair of clamping members made of a physiologically acceptable material are pivotally coupled to the frame for movement apart from each other to an open position and towards each other to a clamping position. The method also includes the steps of placing two concentric purse string sutures into the wall of the blood vessel, cutting a small incision into the blood vessel, inserting the distal tip of the cannula tube through the incision into the blood vessel, tightening the purse string sutures so as to seal the blood vessel wall around the cannula distal tip to prevent the escape of blood from the blood vessel, and clamping a section of the blood vessel by compressing the blood vessel section with the clamping members with pressure sufficient to occlude blood flow through the section.

BRIEF DESCRIPTION OF THE DRAWINGS

These and other features of the invention will now be described with reference to the drawings of a preferred embodiment, which are intended to illustrate and are not to limit the invention, and in which.

DETAILED DESCRIPTION OF PREFERRED EMBODIMENTS

Figure 1:
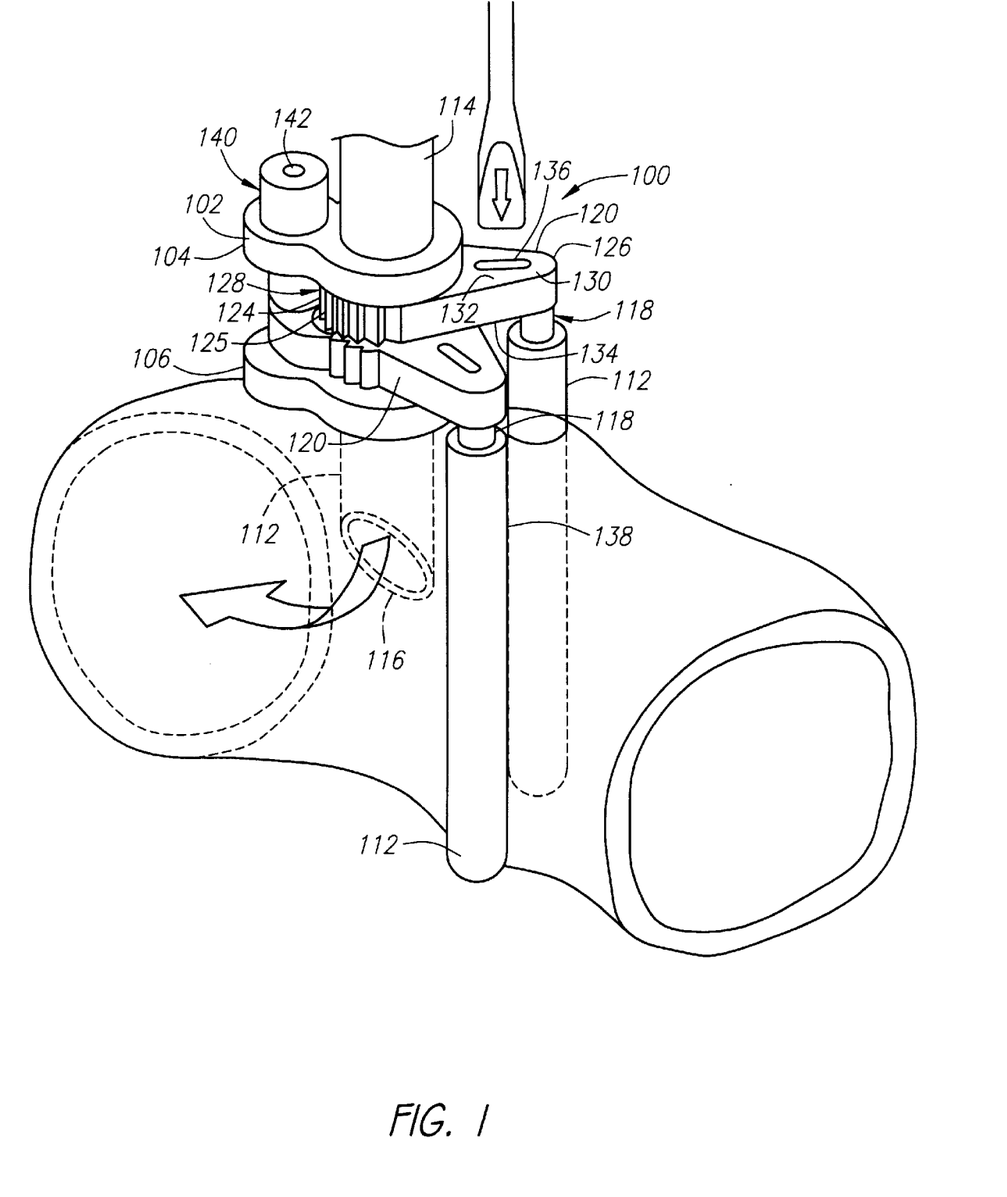
FIG. 1 is a perspective view of an integrated cannula and vascular clamp assembly constructed in accordance with an embodiment of the invention, and shows the assembly applied to a vessel.

With reference to FIG. 1, an integrated cannula and vascular clamp assembly, indicated generally by the reference numeral 100 and constructed in accordance with an embodiment of the invention, will now be described. The integrated cannula and vascular clamp assembly 100 is shown applied to the ascending aorta. Although the integrated cannula and vascular clamp assembly 100 and the alternative embodiments of the present invention that follow are described as being applied to the ascending aorta, it will be readily understood by those skilled in the art how the present invention may be applied to other blood vessels, tissue lumens or body organs.

The integrated cannula and vascular clamp assembly 100 includes a support frame 102 with an upper flange 104 and a lower flange 106. The support frame 102 is made of a physiologically acceptable stainless steel, a plastic material or other biocompatible material. The upper flange 104 and the lower flange 106 include respective holes for receiving a distal portion 112 of a cannula tube 114. The cannula tube 114 is preferably made from silicone rubber and reinforced with a wound stainless steel wire embedded in the wall of the cannula tube 114 to provide flexibility, while minimizing the risk of kinking. The distal portion 112 includes a distal tip 116 that is beveled to minimize trauma to the vessel wall upon insertion. The distal portion 112 defines a central longitudinal axis.

The lower flange 106 is positioned a predetermined distance from the distal tip 116 to limit the length of cannula tube 114 which can be inserted into the aorta, and sets or stabilizes the position of the tip within the aorta. It is important to minimize the extent in which the tip of the cannula tube 114 rubs against or contacts a calcified or otherwise diseased interior wall of the aorta in order to minimize the risk of embolism which can lead to stroke.

A pair of substantially parallel clamping members 118 are pivotally coupled to the frame 102 between the upper flange 104 and lower flange 106. The clamping members 118 are made of a physiologically acceptable plastic or stainless steel material. The clamping members 118 each include a pivoting portion 120 and a clamping portion 122.

Each pivoting portion 120 includes a rounded proximal part 124 and a protruding distal part 126. The pivoting portions 120 pivot at the proximal part about an axis that is generally parallel to the axis defined by the distal portion 112 of the cannula tube 114. The pivoting portions 120 include concentric holes or cut-outs (not shown) for receiving the distal portion 112 of the cannula tube 114. The pivoting portions 120 include ratchet-type teeth 125 along part of its periphery. Cooperating locking members or ratch-members (needs a number)cooperate with the ratchet teeth 125 for locking the clamping members 118 in position. Together the ratchet teeth 125 and locking members form a one-way ratchet mechanism, indicated generally by the reference numeral 128, for locking the clamping members 118 in a clamped position. The distal part 126 of the pivoting portion 120 includes a lobed extension 130 with an upper surface 132 and lower surface 134. A narrow slot 136 is located in the upper surface 132 and is adapted to receive a clamp actuator device such as the flat head of a screwdriver-like device or similar device for actuating or manipulating the clamping members 118.

The clamping portions 122 extend perpendicularly from the lower surface 134 of the distal part 126 of the pivoting portion 120. The clamping portions 122 are generally cylindrical and define respective central longitudinal axes which are generally parallel with the axis of the distal portion 112 of the cannula tube 114. The clamping portions 122 may include respective covers or cushions 138 for minimizing any trauma to the vessel. The clamping portions 122 preferably have a length slightly longer than the flattened width of the clamped vessel.

The integrated cannula and vascular clamp assembly 100 includes a quick release mechanism 140 which, here, includes a push button 142. The quick release mechanism 140 is operatively associated with the ratchet mechanism 128 for immediately disengaging the serrated edges 125 and locking members upon actuation by the push button 142. This allows the clamping members 118 to be immediately opened.

The integrated cannula and vascular clamp assembly 100 will now be described in use. After an incision is made in the patient's chest and the pericardium (the protective sac around the heart) has been entered, two concentric purse string sutures are placed into the anterior wall of the ascending aorta just proximal to upstream of the brachiocephalic trunk. A "choker" tube or sleeve is positioned over the trailing ends of the suture threads to act as a tourniquet for tightening the purse string suture.

A small incision is then made through the wall of the aorta in the center of the purse-string sutures. The distal tip 116 of the integrated cannula and clamp assembly 100 is then quickly inserted through that incision into the lumen of the aorta, taking care to minimize the escape of blood from the puncture site. When the distal tip 116 is inserted into the aorta, the clamping members 118 must be in the open, separated position so that clamping portions 122 slide along the sides of the aorta. The purse string sutures are then tightened by means of their respective tourniquets to seal the aortic wall around the cannula tube 114 in order to prevent the escape of blood from the aorta.

Air is then evacuated from the cannula tube 114 as it is joined by a connector to the tubing from the pump-oxygenator. The clamping members 118 are brought together so that the clamping portions 122 occlude the ascending aorta just downstream of the aortic root and upstream of the distal tip 116 to ensure that no blood flows back into the aorta during CPB. The clamping portions 122 are brought together to compress the aorta by inserting the flat head of a screwdriver or similar device into each slot 136, and moving the clamping portions 122 together with a twist of the screwdriver. The use of a remote clamp actuator, coupled to the clamp mechanism by means of a low profile cable mechanism or other equivalent means, is also contemplated.

The ratchet mechanism 128 ensures that the clamping members 118 remain in a closed, clamped position during cardiac procedures, with nothing more than the cannula tube itself protruding from the chest opening. If it becomes necessary for blood flow to occur through the occluded aorta, the quick release mechanism 140 is actuated by pushing the push button 142, allowing the clamping portions 122 to be immediately separated so that they no longer occlude the aorta.

The integrated nature of the assembly 100 reduces the obstructing effect that a separate vascular clamp has on the cardiac procedure.

FIGS. 2–6 illustrate additional embodiments of the integrated cannula and vascular clamp assembly of the present invention. Where appropriate, like reference numbers with an "a," "b," etc. suffix have been used to indicate like parts of the embodiments for ease of understanding.

Figure 2:
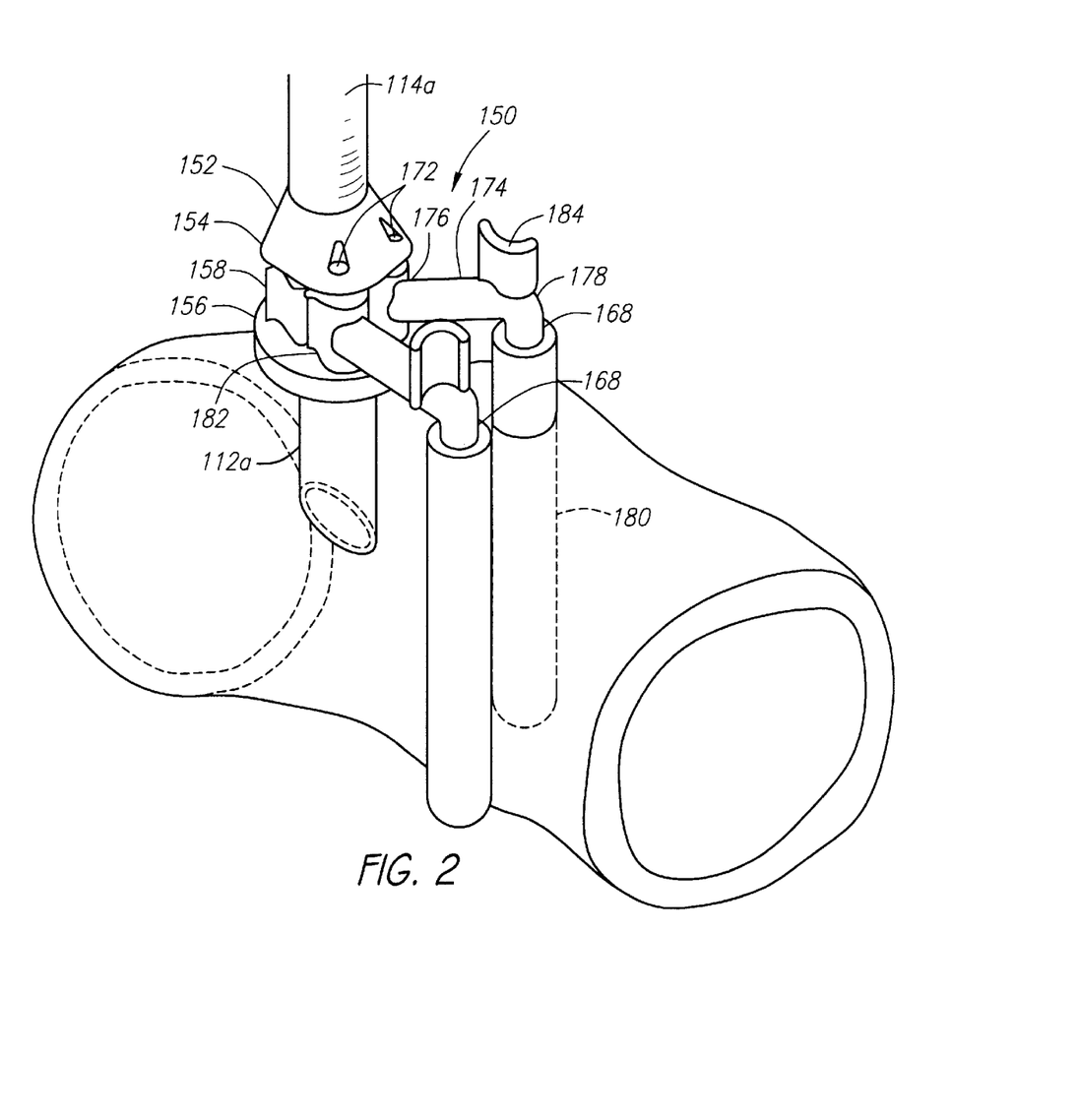
FIG. 2 is a perspective view of an integrated cannula and vascular clamp assembly constructed in accordance with an additional embodiment of the invention, and shows the assembly applied to a vessel.
Figure 3:
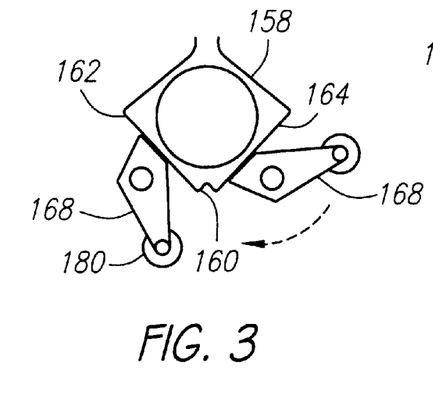
FIG. 3 is a top, cross-sectional view of the spring and over-the-center cams of the integrated cannula and vascular clamp assembly of FIG. 2.

With reference to FIGS. 2, 3 and 4A–4C, an integrated cannula and vascular clamp assembly, constructed in accordance with a further embodiment of the present invention and indicated generally by the reference numeral 150, will now be described. The integrated cannula and vascular clamp assembly 150 includes a support frame 152 with an upper support piece 154 and a lower support flange 156. A flexible spring member 158 is disposed between the upper support piece 154 and the lower support flange 156. The upper support piece 154, lower support flange 156, and spring member 158 include respective holes for receiving the distal portion 112a of the cannula tube 114a. As shown in FIG. 3, the spring member 158 has a generally diamond-shaped cross section, and a front dimple 160 and resilient angled side faces 162, 164.

A pair of clamping members 168 are pivotally coupled to the front of the support frame 152 with pins 172. The clamping members 168 pivot about a central longitudinal axis defined by the pins 172 which is generally parallel to the longitudinal axis of the distal portion 112a of the cannula tube 114a.

Figure 4A:
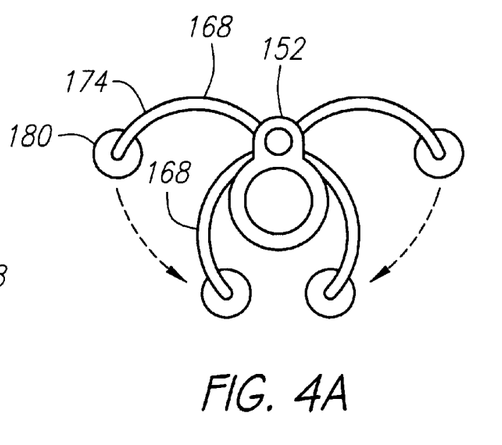
FIGS. 4A–4C are top, cross-sectional views of various embodiments of a cannula frame and clamping members of the present invention, and show alternative locations on the frame where the clamping members may be pivotally coupled to the frame.
Figure 4B:
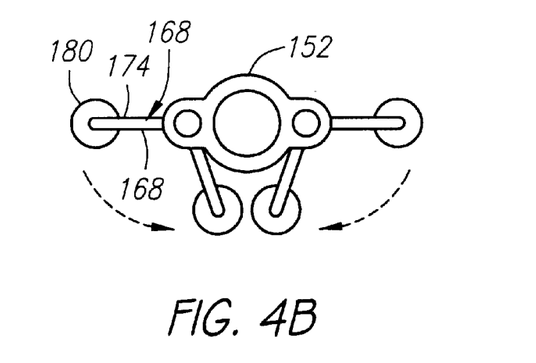
Figure 4C:
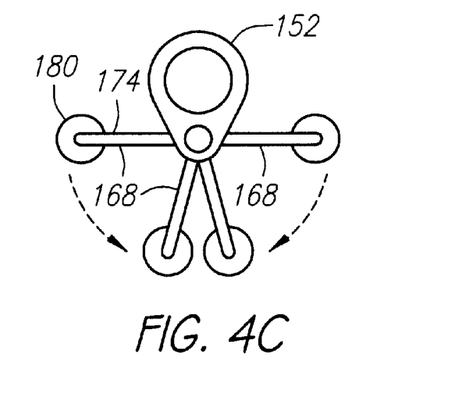

Although the clamping members 168 are shown in FIGS. 2 and 3 separately pivotally coupled to the front of the frame 152, the clamping members 168 may be coupled to the frame in other ways and/or locations on the frame, such as, but not by way of limitation, coaxially coupled at the rear (FIG. 4A), separately coupled at opposing sides of frame 152 (FIG. 4B), or coaxially coupled at the front (FIG. 4C).

Referring to FIG. 2, each clamping member 168 includes a pivoting portion 174 with a proximal part 176 and distal part 178, and a vessel clamping portion 180. The proximate part 176 includes an over-the-center cam 182 with a hole for receiving the pin 172. As shown in FIG. 3, front faces 162 and 164 of the spring member 158 and cam 182 cooperate so that the clamping member 168 is biased to either an open or closed position. The spring member 158 includes a predetermined amount of tension so that proper amount of compression force is imparted to the aorta.

A semi-circular protruding member 184 extends from the distal part 178 of the pivoting portion 120. The protruding members 184 are adapted to receive the ends of a manipulating tool used to move the clamping members 118. In another embodiment, the protruding members 184, have, for example, but not by way of limitation, a circular shape.

The clamping portion 180, which is similar to clamping portion 122 described above in association with FIG. 1, extends perpendicularly from the distal end 178 of the pivoting portion 174. The clamping portions 180 are generally parallel but may have a slight (1 to 5°) non-parallel bias with the distal portions closer together in the opened position. This "re-load" shape will achieve a parallel position when closed on the vessel, as vessel forces are only constrained at the proximal ends of members 180. The integrated cannula and clamp assembly 150 is applied to the aorta in the same manner as assembly 100 described above, except the ends of a manipulation tool, such as forceps or an operator's fingers, are applied to the protruding members 184 for opening or closing the clamping members 168. When the clamping members 168 are rotated, the over-the-center cams 182 and the faces 162, 164 of the resilient spring member 158 cooperate to bias the clamping portion 180 to either an open position or a closed position.

Figure 5:
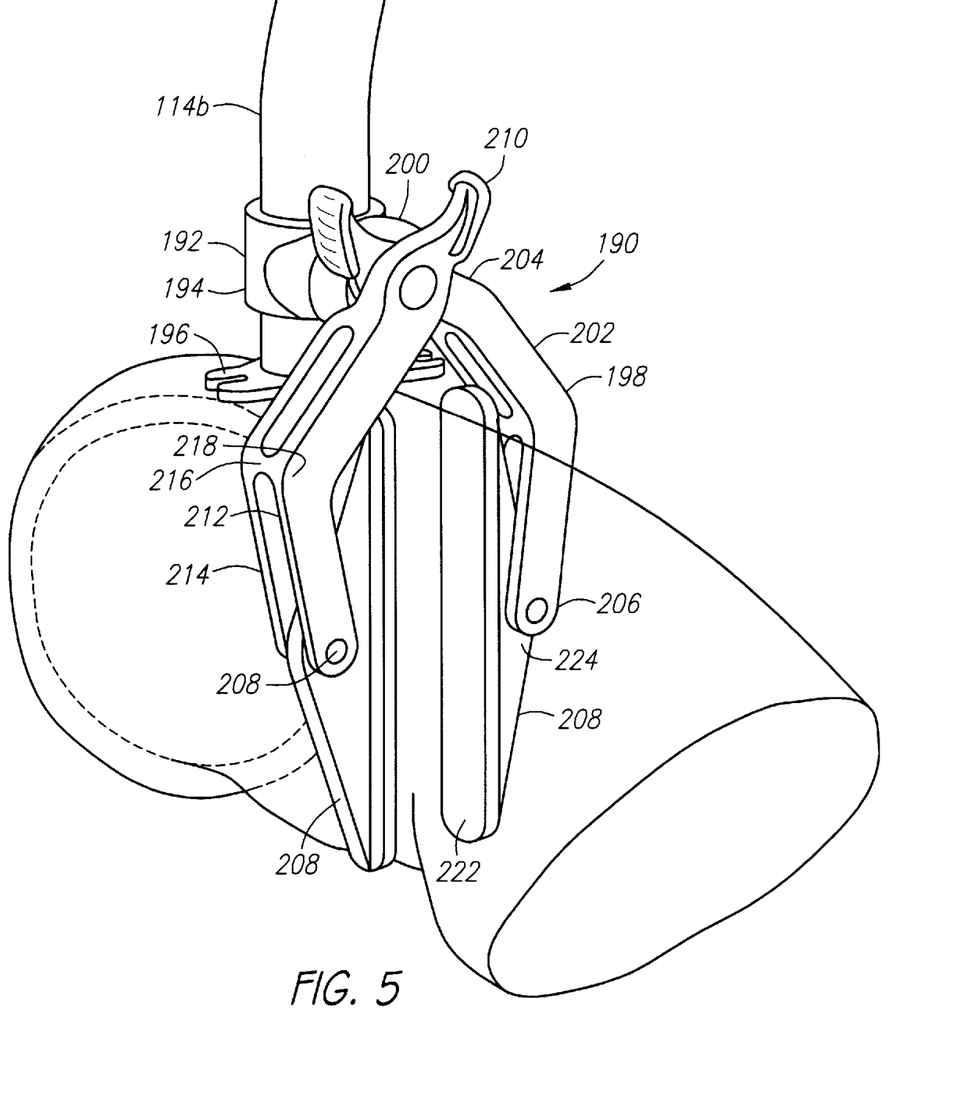
FIG. 5 is a perspective view of an integrated cannula and vascular clamp assembly constructed in accordance with a further embodiment of the invention, and shows the assembly applied to a vessel.

With reference to FIG. 5, an integrated cannula and clamp assembly, indicated generally by the reference numeral 190 and constructed in accordance with an additional embodiment of the invention, is shown. The integrated cannula and clamp assembly 190 includes a support frame 192 with an upper collar 194 and a lower flange 196 that receive a distal portion of a cannula tube 114b. Although the frame 192 is shown as a single-piece construction comprising numerous components, it will be readily understood by those skilled in the art that the frame 192 may comprise a simpler construction such as only the upper collar 194 or the lower flange 196.

A pair of clamping members 198 are pivotally coupled to the support frame 192 with a one-way ratchet mechanism 200. Similar to the one-way ratchet mechanism 128 described above with respect to FIG. 1, the ratchet mechanism 200 includes a serrated or notched member and a locking member (not shown) that cooperate to lock the clamping members 198 into position. The clamping members 198 pivot about an axis that is generally perpendicular to a central axis defined by cannula tube 114b, and, when applied to the aorta, is generally parallel to a central longitudinal axis defined by the aorta section that clamping members 198 are applied to. Although not shown, the integrated cannula and clamp assembly 190 may include a quick release mechanism and actuator similar to the quick release mechanism 140 and push button 142 described above with respect to FIG. 1.

Each clamping member 198 includes a pivoting portion 202 with a proximal part 204 and a distal part 206, and a clamping portion 208. The proximal part 204 has a protruding, striated or knurled pinch member 210 adapted to cooperate with the ends of forceps or the operator's fingers for manipulating the clamping members 198. The pivoting portion 202 has a generally V-shaped configuration defining an obtuse angle. The pivoting portion has a generally solid proximal end that diverges into separated members 212, 214 that are connected by a cross piece 216 at bend 218, and a pivot pin 220 at the distal part 206.

The clamping portion 208 has a generally triangular shape, and includes a base 222 and an apex 224 with an hole for receiving the pivot pin 220. The clamping portion 208 is pivotally coupled to the distal part of the pivoting portion 202 at the apex 224 with the pivot pin 220. The clamping portions 208 are self-aligning and move within a generally longitudinal plane defined by the clamping portions 208.

The integrated cannula and clamp assembly 190 is applied to the aorta in the same manner as that described above, except the clamping members 198 are controlled at the pinch members 210 by an instrument such as forceps or the operator's fingers. The clamping members 198 are locked into place on the aorta through the ratchet mechanism 200. A quick release mechanism (not shown) allows for the immediate opening of the clamping members 198.

The self-aligning feature of the clamping portions 208 causes the forces on the aorta to be distributed as the aorta is occluded. The even distribution of forces is especially important if the aorta is stiffer, thicker, more calcified, etc. in one portion of the aorta wall to be occluded compared to another.

Another benefit of the self-aligning clamping portions 208 is that their distal ends can be spaced a distance apart from each other such that the distance between pins 220 is less than the diameter of the aorta. This reduces the size of the tool and assists in applying the cannula tube 114b to the aorta. Upon application of the integrated assembly 190, the clamping portions 208 simultaneous slide onto the aorta, effectively holding the aorta, and partially occluding it. This effective holding of the aorta by the clamping members 198 helps in guiding the distal tip of the cannula tube 114b through the insertion in the aorta.

Figure 6:
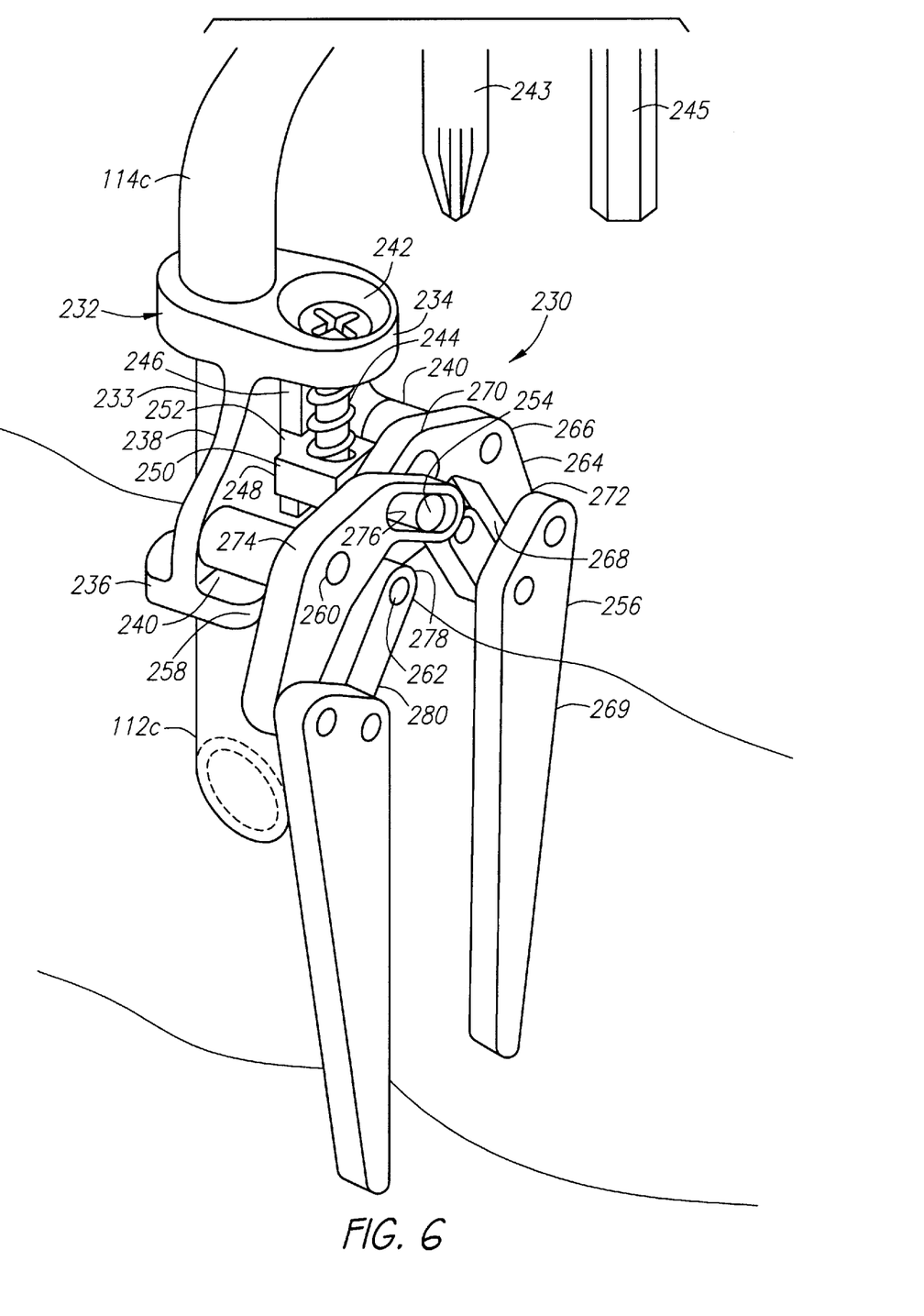
FIG. 6 is a perspective view of an integrated cannula and vascular clamp assembly constructed in accordance with another embodiment of the invention, and shows the assembly applied to a vessel.

With reference to FIG. 6, an integrated cannula and clamp assembly, indicated generally by the reference numeral 230, and constructed in accordance with an additional embodiment of the invention will now be described. The integrated cannula and clamp assembly 230 includes a support frame 232 with main cylindrical vertical body 233, an upper flange 234 and a lower flange 236. A rear part of the upper and lower flanges 234, 236, respectively, and the central lumen of body 233, receives the distal portion 112c of the cannula tube 114c. A pair of tapered ribs 238 extend laterally from the main vertical body 233, from the upper flange 234 to the lower flange 236. A pair of mounting members 240 extend forwardly from a front part of the ribs 238. A recess 242 is located in a front part of the upper flange 234. The main vertical body 233 includes a vertical channel 246.

A threaded member 244 is received within the recess 242 of the upper flange 234. The threaded member 244 shown in FIG. 6 is a screw adapted to receive a phillips head screwdriver 243 for rotation. Because the application of a downward force on the screw may be undesirable during surgery, the rotating member may take a number of alternative forms, such as, but not by way of limitation, a ball socket driver 243, or an attached member integral to 244 with an elongated flexible shaft portion having a ball at a proximal end for imparting rotation.

A reciprocating block member 248 slides in the vertical channel 246. The block member includes a square base 250 with a rearwardly extending sliding member 252 and a forwardly extending pin 254 and a vertical threaded hole through which is accepted the rotatable member 244.

A clamping member 256 is pivotally coupled to the stationary support frame 232 at the mounting member 240 and a lower part 258 of the stationary frame with pins 260, 262, respectively. The clamping member 256 includes a pivoting portion, indicated generally by the reference numeral 264, comprising a first linkage 266 and a second linkage 268, and a clamping portion 269.

The first linkage 266 is curved and includes a proximal part 270 and a distal part 272. The first linkage 266 is pivotally coupled to the mounting member 240 at an bend 274. The proximal parts 270 include respective elongated cut-outs 276, and overlap each other. The elongated cut-outs 276 slidably receive the pin 254 of the reciprocating block member 248.

The second linkage 268 is straight and includes a proximal part 278 and a distal part 280. The proximal part is pivotally coupled to the lower part 258 of the frame 232. Together, the pivoting portions 264 form a four-bar linkage.

The clamping portion 269 is pivotally coupled to the distal parts 272, 280 of the linkages 266, 268, respectively. The clamping portions 269 move generally parallel to each other within a plane defined by the frontal surfaces of the clamping portions 269.

The integrated cannula and clamp assembly 230 is applied to the aorta in the same manner as that described above, except for the manner in which the clamping members 256 are moved. The clamping portions 269 are moved inwardly and outwardly by rotating the threaded member 244. Rotation of the threaded member 244 causes the pin 254 extending from the block member 248 to reciprocate accordingly. As the pin 254 moves, corresponding opening or closing movement is imparted to the clamping portions 269.

For example, if the integrated cannula and clamp assembly 230 is applied to the aorta, and it is desired to occlude the aorta, the threaded member 244 is rotated in a clockwise direction. This causes the pin 254 to rise. As the pin 254 rises, the proximal parts 270 of the first linkage 266 are forced to rise. This causes the clamping members 256 to translate towards each other. Translation of the clamping members 256 towards each other causes the generally parallel clamping portions 269 to close on the aorta until it is occluded. The clamping members 256 are opened by rotating the threaded member 244 in the opposite direction.

It will be readily understood by those skilled in the art, that certain components, aspects, principles, etc., of any of the above-described embodiments, may be applied to other embodiments, such as, but not by way of limitation, the clamp materials, the locking means, the quick release mechanism, the clamping assembly, and the manner in which the size, shape, and configuration of the clamping members are moved. Although this invention has been described in terms of a preferred embodiments, other embodiments apparent to those of ordinary skill in the art are also within the scope of this invention. Accordingly, the scope of this invention is intended to be defined only by the claims that follow.

What is claimed is:

1. An integrated cannula and clamp assembly for delivering fluid to a vessel and temporarily occluding a section of the vessel, the assembly comprising:

a cannula for delivering fluid to a vessel, the cannula including a frame and an elongated cannula tube supported by the frame and having a distal tip, the cannula tube adapted to deliver fluid to the vessel through the distal tip;

a pair of clamping members pivotally coupled to the frame for movement apart from each other to an open position for at least partially surrounding a portion of the vessel section to be occluded and for movement towards each other to a clamping position for compressing the vessel with pressure sufficient to occlude fluid flow through the section.

2. The integrated cannula and clamp assembly of claim 1, further including a quick release mechanism that allows immediate movement of the clamping members upon actuation of said quick release mechanism.

3. The integrated cannula and clamp assembly of claim 1, wherein the clamping members each include a pivoting portion with a proximal part and distal part, each pivoting portion is pivotally coupled to the frame at least one point on the frame, and a clamping portion extending from the distal part of the pivoting portion.

4. The integrated cannula and clamp assembly of claim 1, wherein a portion of the cannula to be near the distal tip defines a central longitudinal axis, the clamping members define respective central longitudinal axes, and the axes of the clamping members are generally parallel with the axis of the cannula tube near the distal tip.

5. The integrated cannula and clamp assembly of claim 1, wherein said cannula frame includes a front portion, a rear portion and side portions, the clamping members are pivotally coupled to the frame at a location selected from the group consisting of the front portion, the rear portion and the side portions.

6. The integrated cannula and clamp assembly of claim 3, further including a spring and cam assembly for biasing the clamping members to the open or the clamping position.

7. The integrated cannula and clamp assembly of claim 6, wherein the spring has a predetermined tension so as to provide the proper amount of clamping force on the blood vessel.

8. The integrated cannula and clamp assembly of claim 6, wherein said actuating means includes a protruding member adapted to receive an end of a pair of forceps.

9. The integrated cannula and clamp assembly of claim 3, further including a ratchet mechanism for locking the clamping portions in the clamping position.

10. The integrated cannula and clamp assembly of claim 9, further including a quick release mechanism, the quick release mechanism disengages the ratchet mechanism upon actuation of said quick release mechanism.

11. The integrated cannula of claim 1 further comprising a means for actuating the clamp members between an open and a closed position.

12. The integrated cannula and clamp assembly of claim 11, wherein said actuating means includes a receptacle on the clamping members adapted to receive an actuator tool.

13. The integrated cannula of claim 11 wherein said actuator tool is hand-held.

14. The integrated cannula and clamp assembly of claim 1, wherein said blood vessel section defines a central longitudinal axis, the clamping members are pivotally coupled to the frame for pivotal movement about at least one axis that is generally parallel to the longitudinal axis of the blood vessel section.

15. The integrated cannula and clamp assembly of claim 12, wherein the clamping portions move within a generally longitudinal plane defined by the clamping portions.

16. The integrated cannula and clamp assembly of claim 12, further including a ratchet mechanism for locking the clamping portions in the clamping position.

17. The integrated cannula and clamp assembly of claim 14, further including a quick release mechanism, the quick release mechanism disengages the ratchet mechanism upon actuation of said quick release mechanism.

18. The integrated cannula and clamp assembly of claim 14, wherein the proximal end of each pivoting portion includes a protruding pinch member.

19. The integrated cannula and clamp assembly of claim 13, wherein the clamping portions are self-aligning.

20. The integrated cannula and clamp assembly of claim 18, wherein each clamping portion is generally triangular in shape and includes an apex, and the clamping portion is pivotally coupled to the distal part of the pivoting portion at the apex.

21. The integrated cannula and clamp assembly of claim 13, wherein the clamping portions are parallel to each other at all time.

22. The integrated cannula and clamp assembly of claim 20, wherein the clamping member includes a four-bar linkage.

23. The integrated cannula and clamp assembly of claim 21, wherein the frame includes an elongated slot, a slidable member including a pin is slidably received in said elongated slot, the proximal ends of said pivoting portions include an elongated cut-out, the pin of the slidable member is slidably disposed within the elongated cut-out, a rotating member is operatively associated with said slidable member so as to move said slidable member upon rotation of said rotating member, and the movement of said slidable member imparts corresponding movement to said four-bar linkage.

24. A method of delivering fluid to a vessel and temporarily occluding a section of the vessel comprising the steps of:

providing an integrated cannula and clamp assembly comprising a cannula for delivering fluid to a blood vessel, the cannula including a frame, an elongated cannula tube supported by the frame and having a distal tip, a pair of clamping members pivotally coupled to the frame for movement apart from each other to an open position and towards each other to a clamping position;

placing at least one concentric purse string sutures into the wall of the blood vessel;

cutting a small incision into the blood vessel;

inserting the distal tip of the cannula tube through the incision into the blood vessel;

tightening the purse string sutures so as to seal the blood vessel wall around the cannula distal tip to prevent the escape of blood from the blood vessel;

clamping a section of the blood vessel by compressing the blood vessel section with the clamping members with pressure sufficient to occlude blood flow through the section.

25. The method of claim 23, further including the steps of providing a quick release mechanism that is operably associated with the clamping members so as to allow immediate opening movement of said clamping members upon actuation of said quick release mechanism, actuating said quick release mechanism, and moving the clamping members to an open position.

* * * * *

UNITED STATES PATENT AND TRADEMARK OFFICE
CERTIFICATE OF CORRECTION

PATENT NO. : 5,928,253
DATED : July 27, 1999
INVENTOR(S) : Benjamin Sherman et al.

It is certified that error appears in the above-identified patent and that said Letters Patent is hereby corrected as shown below:

Column 5,
Line 45, please delete "(needs a number)".

Column 7,
Line 44, please change ""re-load"" to -- "pre-load" --.

Column 9,
Line 34, please change "an bend" to -- a bend --.

Column 10,
Line 9, please change "a preferred embodiments." to --preferred embodiments. --

Column 12,
Line 34, please change "claim 23" to -- claim 24 --.

Signed and Sealed this

Thirty-first Day of July, 2001

*Attest:*

*Attesting Officer*

NICHOLAS P. GODICI
*Acting Director of the United States Patent and Trademark Office*